United States Patent [19]

Guerrero et al.

[11] Patent Number: 5,336,497
[45] Date of Patent: Aug. 9, 1994

[54] COSMETIC COMPOSITION

[75] Inventors: Angel A. Guerrero, Huntington, Conn.; Anthony Vargas, Mahwah, N.J.

[73] Assignee: Elizabeth Arden Co., Division of Conopco, Inc., New York, N.Y.

[21] Appl. No.: 140,622

[22] Filed: Oct. 21, 1993

Related U.S. Application Data

[63] Continuation of Ser. No. 5,200, Jan. 15, 1993, abandoned, which is a continuation of Ser. No. 867,940, Apr. 13, 1992, abandoned.

[51] Int. Cl.$^5$ .............................................. A61K 7/00
[52] U.S. Cl. ...................................... 424/401; 424/70; 514/944; 514/975
[58] Field of Search .................. 424/70, 401; 514/944, 514/975

[56] References Cited

U.S. PATENT DOCUMENTS

| | | | |
|---|---|---|---|
| 4,423,041 | 12/1983 | Clum et al | 514/63 |
| 4,717,498 | 1/1988 | Maxon | 252/174.15 |
| 4,777,277 | 10/1988 | Colas et al. | 556/419 |
| 4,849,127 | 7/1989 | Maxon | 252/174.22 |
| 5,093,112 | 3/1992 | Birtwistle et al. | 424/70 |

FOREIGN PATENT DOCUMENTS

| | | |
|---|---|---|
| 0117135 | 8/1984 | European Pat. Off. . |
| 0473508 | 3/1992 | European Pat. Off. . |
| WO90/13283 | 11/1990 | PCT Int'l Appl. . |

OTHER PUBLICATIONS

Product Brochure #TDS-114 entitled "Introducing Pemulen Polymeric Emulsifiers".
Product Brochure #TDS-117 entitled "Skin Care Products Formulated with Pemulen Polymeric Emulsifiers".
Product Brochure #TDS-118 entitled "Fragrance Products Formulated with Pemulen Polymeric Emulsifiers".

Primary Examiner—Thurman K. Page
Assistant Examiner—Jyothsna Venkat
Attorney, Agent, or Firm—Milton L. Honig

[57] ABSTRACT

A cosmetic composition is provided that includes a silicone copolyol sulfosuccinate and an amphoteric surfactant, preferably in clear gel form. The amphoteric surfactant may be selected from the group consisting of alkyl betaine, alkylamido betaine and combinations thereof.

5 Claims, No Drawings

COSMETIC COMPOSITION

This is a continuation application of Ser. No. 08/005,200, filed Jan. 15, 1993, now abandoned, which is a continuation of Ser. No. 07/867,940 filed Apr. 13, 1992, now abandoned.

BACKGROUND OF THE INVENTION

FIELD OF THE INVENTION

The invention concerns a cosmetic composition for application to the human skin.

RELATED ART

Considerable foreign material normally reaches and attaches to the skin. This foreign material may include both exogenous and autochthonous soils. The exogenous soils include those which reach the skin unintentionally, or that which is intentionally applied, such as ointments or cosmetics. Autochthonous soils are the products of excretion of the sebaceous, eccrine and apocrine glands. Cells and flakes of the cornified epithelium are also being shed continuously. Both society and health demand that these soils be removed from time to time. For abnormal skin, there must also be removal of pus, blood cells, serous exudates and crusts.

Bathing with a soap bar is the usual manner for removing foreign material from the skin. Soap is, however, harsh. Neither does soap provide the softening, lubricating, protective or even exfoliating properties that are necessary for full treatment of the skin. A body rub formulation applied after bathing may provide the aforementioned properties missing from a mere treatment with soap.

A most important component of any body rub is that of a cleansing agent, especially a surfactant that is mild. Illustrative is U.S. Pat. No. 4,717,498 and U.S. Pat. No. 4,849,127, both to Maxon, which describe the use of dimethicone copolyol sulfosuccinate compounds as mild, foam-enhancing surfactants. Somewhat similar organosilicone sulfosuccinates are reported in U.S. Pat. No. 4,777,277 (Colas et al).

It is an object of the present invention to provide a cosmetic composition of excellent mildness for conditioning skin.

Another object of the present invention is to provide a cosmetic composition for use as a body rub to exfoliate skin.

Still a further object of the present invention is to provide a body rub exfoliator that is in the form of a clear gel so as to be aesthetically-pleasing to a consumer.

These and other objects, features and advantages of the present invention will become more readily apparent through consideration of the following summary, detailed description and examples which follow.

SUMMARY OF THE INVENTION

A cosmetic composition is provided comprising:
(i) from about 0.01 to about 30% by weight of a silicone copolyol sulfosuccinate;
(ii) from about 0.01 to about 30% by weight of an amphoteric surfactant; and
(iii) from about 1 to about 99.95% of a pharmaceutically acceptable vehicle.

DETAILED DESCRIPTION

Now there has been identified a body rub cosmetic composition exhibiting excellent conditioning properties and possessing consumer pleasing aesthetics. The composition is based upon silicone copolyol sulfosuccinate compounds in combination with an amphoteric surfactant. The composition can be formulated into a clear gel.

According to the invention, there is required a silicone copolyol sulfosuccinate of the formula:

$$(CH_3)_3SiO \left[ \begin{array}{c} CH_3 \\ | \\ SiO \\ | \\ CH_3 \end{array} \right]_x \left[ \begin{array}{c} CH_3 \\ | \\ SiO \\ | \\ R \\ | \\ O \quad O-M \\ | \quad | \\ O=C \quad C=O \\ | \quad | \\ MO_3S-C-CH_2 \\ | \\ H \end{array} \right]_y Si(CH_3)_3$$

wherein R is an alkylene oxide polymer; M is a cation selected from the group consisting of hydrogen, alkali metal, alkaline earth metal, ammonium and alkanolammonium ions, x and y range in value so as to produce a compound with an equivalent weight between 700 and 1600 grams. R may be further defined as a polymer of ethylene or propylene oxide in the following forms:

$$(-CH_2-CH_2O)_a H;$$

$$(-CH-CH_2O)_b H; \atop | \atop CH_3$$

wherein a and b range in value from 1 to 30; and $$(-CH_2-CH_2O)_a-(CH-CH_2O)_b H \atop | \atop CH_3$$

wherein a and b may range in value from 0 to 30.

A related silicone copolyol sulfosuccinate structure according to the present invention is represented by the formula:

$$\left[ (CH_3)_3SiO \left[ \begin{array}{c} CH_3 \\ | \\ SiO \\ | \\ CH_3 \end{array} \right]_x \left[ \begin{array}{c} CH_3 \\ | \\ SiO \\ | \\ R \\ | \\ O \quad O-M \\ | \quad | \\ O=C \quad C=O \\ | \quad | \\ HO_3S-C-CH_2 \\ | \\ H \end{array} \right]_y Si(CH_3)_3 \right] X$$

wherein X is an amine group obtained from alcohol amines, ethoxylates or propoxylates, preferably derived from the group consisting of monoethanolamine, diethanolamine, triethanolamine, monoisopropanolamine or diglycolamine.

A further related silicone copolyol sulfosuccinate structure according to the present invention is represented by the formula:

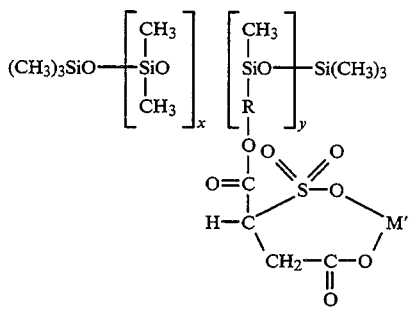

wherein M' is an alkaline earth metal, for example, calcium, magnesium or barium, rather than an alkali metal.

A still further related silicone copolyol sulfosuccinate structure according to the present invention is represented by the following formula:

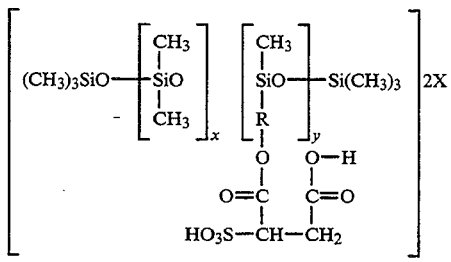

wherein X is an amine group as described above and obtained from sulfite salts containing the amine group.

The silicone copolyol sulfosuccinates of the present invention are generally prepared by reacting the ethoxylated polyether side chains of dimethicone copolyol with maleic anhydride to form a monoester and then converting the monoester to sulfosuccinate by sulfonation of the double bond with a metallic sulfite. Metallic sulfite and amine salts may also be used either alone or in combination for sulfonation of the double bond. The resulting sulfosuccinate is a silicone-based surfactant which exhibits highly improved mildness and foam stabilizing properties.

Commercially, the silicone copolyol sulfosuccinates are available from the McIntyre Chemical Company under the trademark of Mackanate DC-30 and DC-30A.

Amounts of the silicone copolyol sulfosuccinate for use in compositions of the present invention may range from about 0.01 to about 30%, preferably from about 0.5 to about 20%, optimally between about 5 and about 10% by weight.

Another important component of compositions according to the present invention is that of an amphoteric surfactant. The surfactant may be selected from alkyl and alkylamido betaines, sultaines and from acylated α-amido acids. Suitable examples include:

Alkyl betaines having the structure:

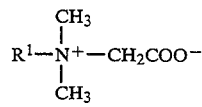

wherein $R^1$ is $C_{10}$–$C_{18}$ alkyl. An example of alkyl betaines having the structure is lauryldimethyl betaine (e.g. Empigen BB, available from Albright & Wilson).

Alkylamidopropyl betaines, having the structure:

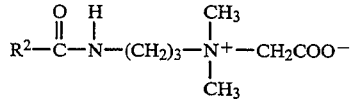

wherein $R^2$ is $C_{10}$–$C_{18}$ alkyl. An example of alkylamidopropyl betaines of the above structure is cocoamidopropyl betaine (e.g. Velvetex BK-35, available from Henkel and Tegobetaine L7, available from Goldschmidt).

Sultaines having the structure:

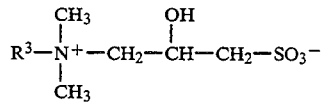

wherein $R^3$ is chosen from $C_{12}$–$C_{18}$ alkyl or alkylamido. An example of sultaines having the above structure is cocoamidopropylhydroxysultaine (e.g. CYCLOTERIC BET-CS, available from Alcolac).

Particularly preferred as the amphoteric surfactants are the alkylamidopropyl betaines.

Amounts of the amphoteric surfactant according to the present invention may range from about 0.01 to about 30%, preferably from about 0.5 to about 10%, optimally between about 1 and about 5% by weight.

As the pharmaceutically acceptable vehicle, it is particularly advantageous to utilize a hydroxylic substance such as water. The vehicle may be present in amounts anywhere from about 1 to about 99.95%, preferably between about 40 and about 85%, optimally between about 50 and 70% by weight.

Vehicles other than water that can be used in compositions according to the invention can include liquids or solids such as emollients, solvents, humectants, thickeners and powders. Examples of each of these types of vehicles, which can be used singly or as mixtures of one or more vehicles, are as follows:

emollients, such as stearyl alcohol, oleyl alcohol, octadecan-2-ol, isocetyl alcohol, eicosanyl alcohol, behenyl alcohol, glyceryl monolaurate, glyceryl monoricinoleate, glyceryl monostearate, propane-1,2-diol, butane-1,3-diol, docosan-1,2-diol, mink oil, cetyl alcohol, isopropylisostearate, stearic acid, isobutyl palmitate, isocetyl stearate, isopropyl laurate, hexyl laurate, decyl oleate, cetyl palmitate, silicone oils such as dimethylpolysiloxane, di-n-butyl sebacate, isopropyl myristate, isopropyl palmitate, isopropyl stearate, butyl stearate, lanolin, cocoa butter, corn oil, cottonseed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petrolatum, mineral oil, butyl myristate, isostearic acid, stearic acid, palmitic acid, isopropyl linoleate, lauryl lactate, myristyl lactate, decyl oleate and myristate;

solvents such as ethyl alcohol, methylene chloride, isopropanol, acetone, castor oil, ethylene glycol monoethyl ether, diethylene glycol monobutyl ether, diethylene glycol monoethyl ether and dimethyl sulphoxide;

humectants such as glycerin, sorbitol, polyethylene glycol, triethylene glycol, soluble collagen, and gelatin;

powders such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminum silicate, fumed silica, carboxyvinyl polymer, sodium carboxymethyl cellulose and alkyl celluloses.

Although the cosmetic composition of this invention may be in liquid, powder, stick or other form, it is especially desirable to utilize a gel state. In fact, compositions of this invention are intended to be clear gels. Clarity is defined by its usual dictionary definition. Thus, a clear formulation, like glass, allows ready viewing of objects behind it. By contrast, a translucent formulation, although allowing light to pass through, causes the light to be so scattered as by a very small proportion of crystals or insolubles, that it will be impossible to clearly identify objects behind the translucent formulation. One test for clarity is to place a newspaper behind a sample 10 cm thick. If one is able to read print through the samples, then the composition is considered to be clear.

A further useful component may be a co-emulsifier for use with the sulfosuccinate. Examples of such materials are the acrylates/C10-C30 alkyl acrylate cross-polymers that are commercially available from the B.F. Goodrich Company under the trademark Pemulen TR-2 ®. Another co-emulsifier also useful in the present invention is that of Polysorbate 20. Amounts of such materials may range each from about 0.1 to about 5% by weight.

When compositions of the present invention are used as exfoliant products, they may include such substances as hydrogenated jojoba oil, preferably in the form of wax beads. Of course, inorganic salts such as silicas, carbonates, phosphates, bromides and halides may also be utilized for such purpose. Normally present in compositions of this invention are preservatives, examples of which include methyl paraben, propyl paraben, imidazolidinyl urea, sodium dihydroxyacetate, benzyl alcohol, 2-phenoxyethanol, tetrasodium edetate and combinations thereof. Preservatives will usually be present in amounts ranging from about 0.5 to about 3% by weight of a composition.

Other adjunct minor components may also be incorporated into the cosmetic compositions. These ingredients may include coloring agents, opacifiers and perfumes. Amounts of these materials may range anywhere from about 0.001 up to 20% by weight.

The following examples will more fully illustrate the embodiments of this invention. All parts, percentages and proportions referred to herein and in the appended claims are by weight unless otherwise indicated.

EXAMPLE 1

Illustrative of the present invention is a sea salt body rub in the form of a gel having the formula listed below:

| Ingredients | Weight % |
| --- | --- |
| Deionized water | 70.3850 |
| Disodium dimethicone copolyol sulfosuccinate | 10.0000 |
| Jojoba beads (28/60 mesh) | 4.0000 |
| Cocamidopropyl betaine | 3.0000 |
| Butylene glycol | 3.0000 |
| Polysorbate 20 | 3.0000 |
| Triethanolamine, 99% | 1.9000 |
| Acrylates/C10-C30 Alkyl Acrylate Cross-polymer | 1.4000 |
| Soothiplex 173 | 1.0000 |
| 2-Phenoxyethanol | 0.7000 |
| Benzyl alcohol NF | 0.5000 |
| Fragrance | 0.4500 |
| Methylparaben | 0.2000 |
| Seamollient | 0.1500 |
| Tetrasodium edetate | 0.1150 |
| Propylparaben | 0.1000 |
| Sea Salt | 0.1000 |

EXAMPLE 2

This Example evaluates the effect upon replacing cocoamidopropyl betaine of Example 1 with other surfactants.

Three expert panelists were chosen for the evaluation. Each of the panelists was asked to wet the backs of their hands thoroughly prior to applying the test product. One gram of product was dispensed onto the back of the hands. A control was applied on one hand and a test product on the other hand. After application, the products were rubbed onto the skin so as to cover all of the test areas. Panelists were instructed to rub their hands for one minute. Excess product was removed with water and the test areas were patted dry. Products were evaluated on the basis of skin conditioning and afterfeel on the skin. Products were coded so that the panelists did not know which product they were applying.

TABLE I

| Effect of Different Surfactants Upon Skin Conditioning | | | |
| --- | --- | --- | --- |
| | Panelist | | |
| Surfactant | No. 1 | No. 2 | No. 3 |
| Cocoamphocarboxyglycinate | − | − | − |
| Sodium lauriminodipropionic acid | − | − | − |
| Triethanolamine cocoyl glutamate | − | − | − |
| Cocoamidopropyl betaine | + | + | + |

Table I records the results wherein (+) indicates superior conditioning while the (−) indicates inferior conditioning. From Table I it is evident that superior conditioning was achieved only by the combination of cocoamidopropyl betaine with Mackanate DC-30. In a further experiment when Mackanate DC-30 was replaced by an amphoteric surfactant alone, the resulting conditioning was inferior.

EXAMPLE 3

This Example evaluates the effectiveness of various sulfosuccinates. Again, the base formula of Example 1 and same evaluation procedures as Example 2 were herein utilized. Table II sets forth the results.

TABLE II

Effect of Various Anionic Surfactants on Skin Conditioning

| Surfactant | Panelist No. 1 | No. 2 | No. 3 |
|---|---|---|---|
| Disodium laureth sulfosuccinate | − | − | − |
| Triethanolamine lauryl sulfate | − | − | − |
| Dimethicone copolyol sulfosuccinate | + | + | + |

From the results of Table II, it can be seen that only dimethicone copolyol sulfosuccinate is effective to produce a high degree of skin conditioning. The conditioned feel is accomplished through combination with the use of cocamidopropyl betaine.

In a test wherein the anionic surfactant (i.e. Mackanate DC-30) was replaced by Dow Corning 193 (dimethicone copolyol), there resulted a grossly incompatible emulsion that could not be tested for conditioning.

The foregoing description and examples illustrate selected embodiments of the present invention. In light thereof, various modifications will be suggested to one skilled in the art, all of which are within the spirit and purview of this invention.

What is claimed is:

1. A skin-conditioning cosmetic composition comprising:
   (i) from about 0.01 to about 30% by weight of dimethicone copolyol sulfosuccinate;
   (ii) from about 0.01 to about 30% by weight of cocamidopropyl betaine; and
   (iii) from about 1 to about 99.95% of a pharmaceutically acceptable vehicle.

2. A cosmetic composition according to claim 1 in the form of a clear gel.

3. A cosmetic composition according to claim 2 wherein the clear gel contains opaque beads.

4. A clear gel skin conditioning cosmetic composition comprising:
   (i) from about 0.5 to about 20% by weight of dimethicone copolyol sulphosuccinate;
   (ii) from about 0.5 to about 10% by weight of cocamidopropyl betaine; and
   (iii) from about 1 to about 99.95% of a pharmaceutically acceptable vehicle.

5. The composition according to claim 4 wherein the dimethicone copolyol sulphosuccinate is present in an amount from 5 to 10% and the cocamidopropyl betaine is present in an amount from 1 to 5% by weight.

* * * * *